(12) United States Patent
Singh

(10) Patent No.: US 6,994,667 B2
(45) Date of Patent: Feb. 7, 2006

(54) METHOD AND APPARATUS FOR FACILITATING UROLOGICAL PROCEDURES

(76) Inventor: Errol O. Singh, 1988 Cambridge Blvd., Upper Arlington, OH (US) 43221

( * ) Notice: Subject to any disclaimer, the term of this patent is extended or adjusted under 35 U.S.C. 154(b) by 4 days.

(21) Appl. No.: 10/453,770

(22) Filed: Jun. 3, 2003

(65) Prior Publication Data

US 2004/0254422 A1 Dec. 16, 2004

Related U.S. Application Data

(63) Continuation-in-part of application No. 09/480,347, filed on Jan. 10, 2000, now Pat. No. 6,599,237.

(51) Int. Cl.
*A61B 1/00* (2006.01)

(52) U.S. Cl. ............. 600/105; 600/114; 600/135
(58) Field of Classification Search ............ 600/105, 600/109, 114–116, 135; 604/164.05, 164.03, 604/161
See application file for complete search history.

(56) References Cited

U.S. PATENT DOCUMENTS 3,496,930 A * 2/1970 Wappler .................. 600/135
4,612,939 A * 9/1986 Robertson ................ 600/587
4,738,659 A * 4/1988 Sleiman ................ 604/103.09

* cited by examiner

*Primary Examiner*—Beverly M. Flanagan
(74) *Attorney, Agent, or Firm*—James V. Harmon

(57) ABSTRACT

A flexible direct vision fiberoptical viewing cable is placed within a urinary catheter with its tip located at a distal end of the catheter such that the surfaces of the distal end of both the viewing cable and the catheter are aligned so as to fit together in such a way as to form a composite smoothly curved surface to facilitate negotiating obstructions. The cable is maintained in this position within the catheter with the surfaces that comprise the tip of the instrument, maintained in alignment. The urethra is then viewed therethrough during all or part of the insertion procedure for observing and identifying obstructions that may be present and thereafter the fiberoptic cable is withdrawn while allowing the catheter to remain in place within the urethra.

Another form of instrument includes a working sheath and an obturator. A method is also described for facilitating endoscopic examination and surgical procedures through the sheath.

34 Claims, 8 Drawing Sheets

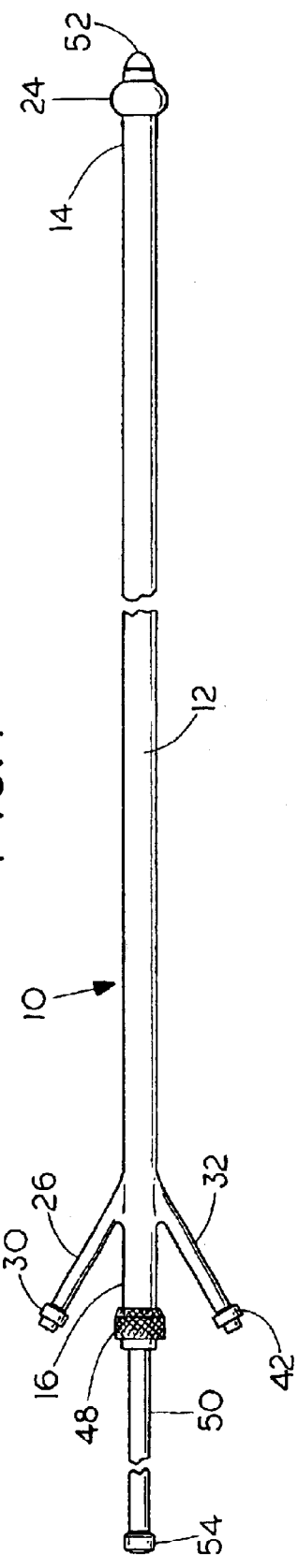
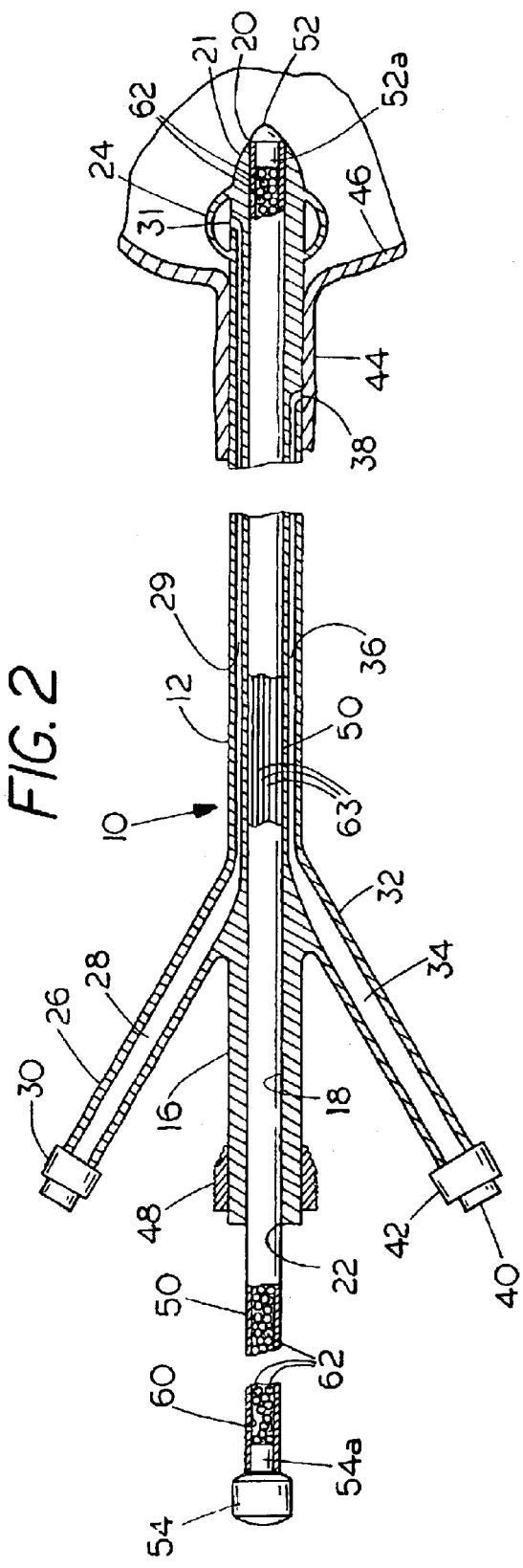

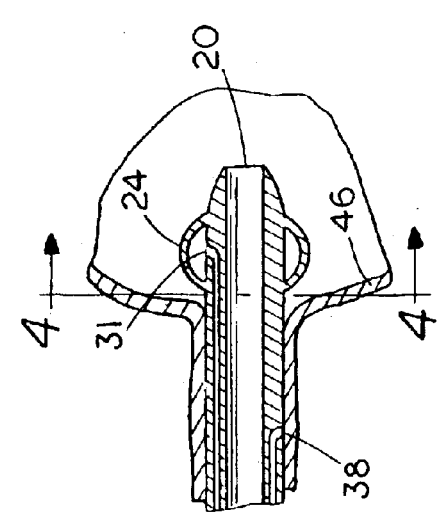
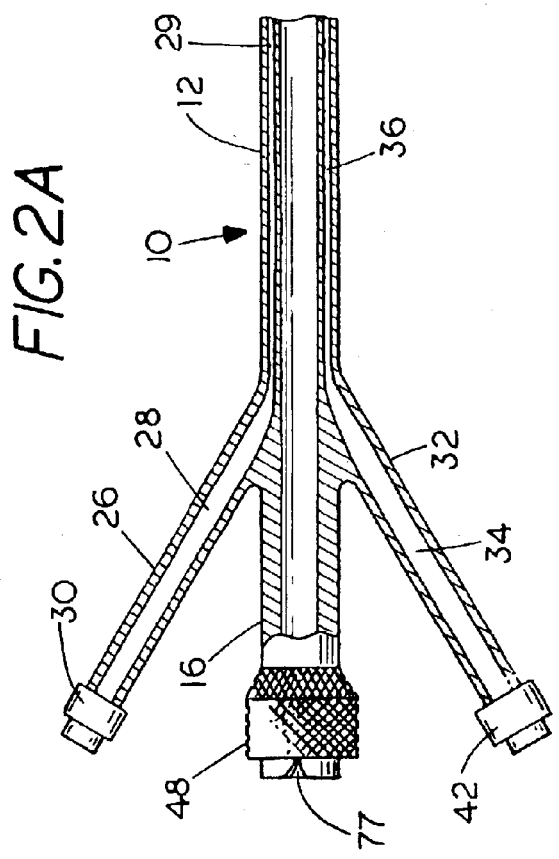
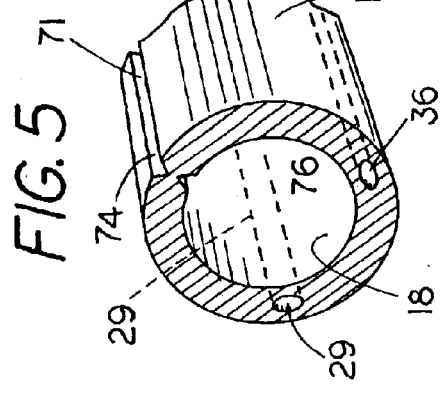
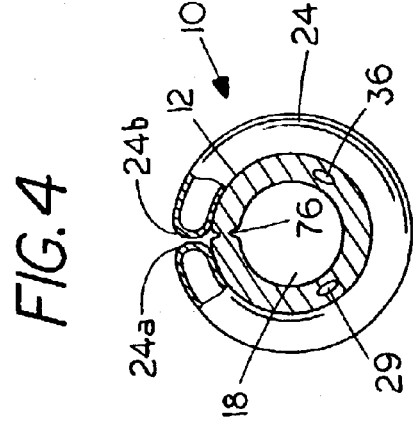
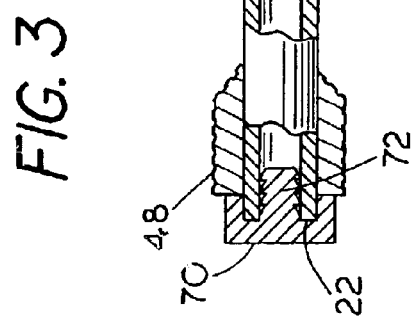

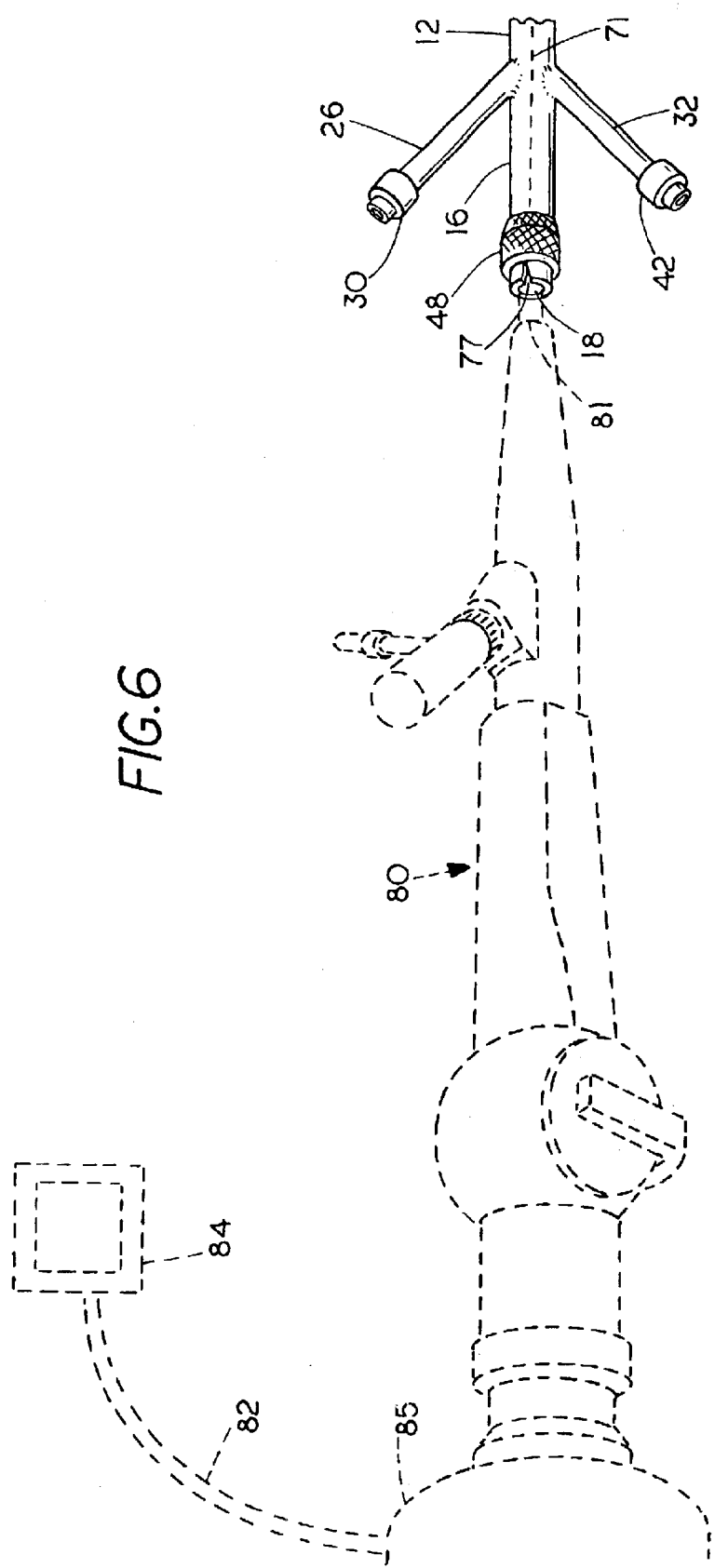

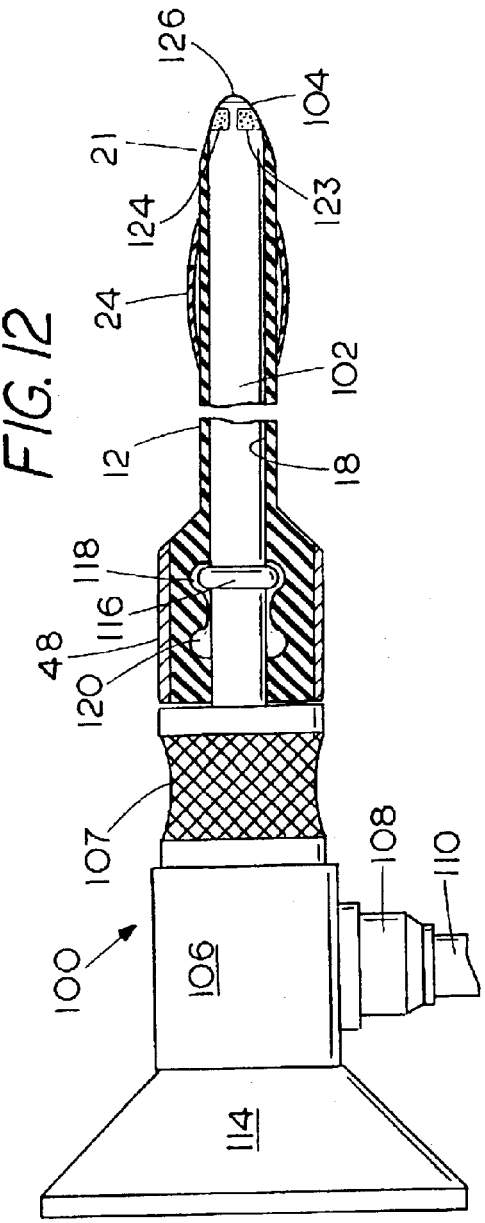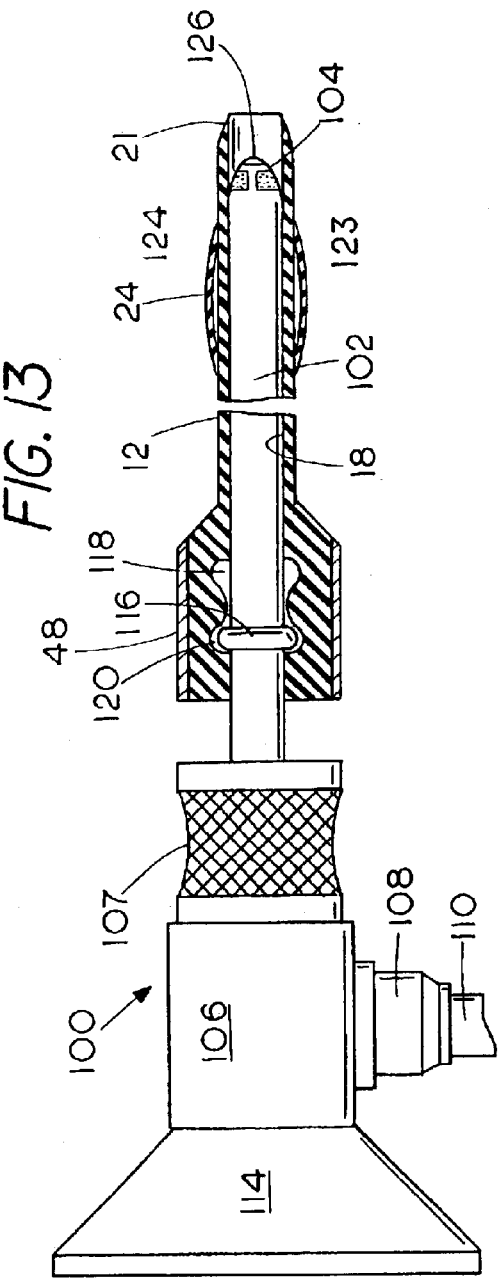

METHOD AND APPARATUS FOR FACILITATING UROLOGICAL PROCEDURES

This is a continuation-in-part of application Ser. No. 09/480,347 filed Jan. 10, 2000 now U.S. Pat. No. 6,599,237.

FIELD OF THE INVENTION

This invention relates to the medical art and more particularly to a method and apparatus for facilitating urological procedures.

BACKGROUND OF THE INVENTION

One of the most common urological procedures, both historically and in current practice, is the placement of a catheter in the urethra for the purpose of draining urine or fluid, to diagnose problems or to maintain anatomic continuity. This procedure is performed by inserting the catheter manually while noting any resistance to forward movement as shown by a failure of the catheter to slide smoothly into the urethra. While most placements proceed without problems, typically about ten percent of urinary catheter placements are difficult, causing a substantial burden on the delivery of effective care through the healthcare system. The most common problem is tetany, a spasm of the external urinary sphincter or stricture of the urethra. Stones, and even clots descending from the bladder, also constitute urethral obstructions. In addition, urethral lumen calibers vary considerably, and particularly with urethritis, BPH, urethritis stricture disease and prostate disorders in males. The cost to the healthcare system, hospitals, clinics and doctors' offices is substantial. In addition, the delay in servicing urological catheter patients in a timely manner constitutes poor medical efficiency, delivery and control. When difficulty is encountered, the resulting frustration among healthcare professionals, especially nurses, physician extenders and physician assistants, creates a very real feeling of ineffectiveness on the part of these healthcare workers, to say nothing of the dissatisfaction on the part of the patients caused by the delay and added discomfort. While the dollar cost to the healthcare system is not the only concern, such elements as added labor and material costs, time delays for patient rectification, excess space and equipment required, catheter kit value, nurse technician and physician costs constitute an expense to the healthcare system of surprising proportions. The best available current data indicates about 150,000 urinary catheter placements are made in the United States per day. Of these, about 15,000 are difficult. From this data it can be calculated that the cost to the healthcare system for additional services by healthcare professionals in the United States is over $700 million dollars per year. Moreover, the additional space and equipment amounts to at least $800 million per year for a total added cost of about $1.5 billion per year.

Accordingly, an important object of the present invention is to virtually eliminate these additional costs, greatly improve patient comfort and satisfaction, as well as shortening the time required for catheter placement while adding only a relatively small cost to the equipment required.

Another more specific object of the invention is to eliminate or drastically reduce problems associated with difficult urethral catheter passage including the formation of iatrogenic trauma strictures, urethral bleeding, urethral mucosal lining tears, patient pain or discomfort, scar tissue formation, treatment delay, increased infection potential, and inappropriate use of antibiotic which may enhance a recalcitrant immune strain modification of the offending organism.

A further specific object of the invention is to provide an apparatus and method for safely passing a catheter through the urethra of both male and female human patients with a provision for enabling healthcare workers such as nurses and physician's assistants who are not board certified urologists to negotiate most obstructions in a safe, efficient and timely manner without the need of a cystoscope.

In several kinds of surgical operations, e.g., urological procedures, it is the current practice to insert and remove various instruments through the urethra several times during a single surgical operation. The repeated insertion and removal of instruments often requires a significant amount of force. This can of course traumatize the tissue. It is therefore another object of the present invention to eliminate the need for inserting and removing a series of surgical instruments by passing them through an opening in the body in a manner that can cause discomfort or injure the tissue and in that way reduce the possibility of bleeding, trauma, inflammation; infection, false passage, and long-term complications such as scarring.

In addition, the manipulation of a surgical instrument or other object that is partially or completely inserted into the body can also result in damage to the surrounding tissue. A more specific object of the invention is to minimize the possibility of damaging the tissue through either the manipulation or the repeated insertion and removal of instruments that have to be used in succession to complete a surgical operation: For example, in many urologic procedures a cystoscope is inserted blindly or under direct vision for evaluation and diagnosis. The cystoscope is frequently removed and another instrument then inserted for lavage, cauterization, extraction or surgery. A series of such instruments are usually inserted in a logical sequence. Finally, at the conclusion of the endoscopic or percutaneous procedure, it is frequently necessary to insert a catheter as a percutaneous drain or for drainage of the bladder or as a post-op drain. The insertion and removal of each of these other instruments increases the chances for traumatizing or injuring surrounding tissue or even creating a false passage and losing access. Moreover, each time a body orifice, i.e., oral cavity, urinary, gastrointestinal tract or other opening is manipulated, the potential for bacteremia is increased. In short, tissue trauma can result from retrograde or antegrade passage instrumentation or removal of foreign bodies. Moreover, many endoscopic, percutaneous or laparoscopic instruments have a relatively small diameter working channel which limits the size of biopsy specimens. The small size limits the removal of such specimens or foreign bodies by necessitating multiple insertions and withdrawals. This prolongs the operation and is an additional source of tissue trauma. Finally, when one instrument is removed and replaced by a second instrument, positioning the distal end of the second instrument is inexact because there is nothing present to locate the second instrument at a predetermined stop point with respect to the position taken by the previous instrument.

While it is known in the art to use a sheath to facilitate the insertion of a small catheter into the body, as described for example in U.S. Pat. Nos. 4,581,025 and RE31,855, no provision is made for accommodating a series of surgical instruments including endoscopes, cauteries, or instruments used in removing tissue for biopsy. Moreover, no provision is made for holding the patented sheath in place nor is there any provision for introducing anesthetic or medication. Accordingly, it is a more specific object of the invention to provide a method and surgical instrument that can be placed percutaneously or transurethrally for facilitating both endoscopic surgery or cystoscopic procedures so as to ease the successive placement, manipulation and removal of various surgical instruments including relatively bulky or rigid instruments such as endoscopes, cautery instruments, cold knife scalpel instrument, and biopsy instruments without increasing the likelihood of bleeding, trauma, inflammation and long-term complications. Another object of the invention is to provide such an instrument with a provision for holding itself securely in place during use while permitting introduction of fluids, e.g., for irrigating the tissue or for anesthesia, etc., and for accommodating instruments that are larger than the lumen of the working sheath. Yet another object of the invention is to provide a method for using such an instrument.

These and other more detailed and specific objects of the present invention will be better understood by reference to the following figures and detailed description which illustrate by way of example of but a few of the various forms of the invention within the scope of the appended claims.

SUMMARY OF THE INVENTION

Briefly, in accordance with one aspect of the invention, a flexible direct vision viewing instrument or viewer, e.g., having fiberoptic shaft or cable, is placed within a urinary catheter with its tip located at a distal end of the catheter so that the surfaces at the distal tip of both the viewing cable and the catheter are aligned, i.e., are flush, to fit together in such a way as to form a smoothly curved end surface for negotiating obstructions as easily as possible. The cable is maintained in this position within the catheter by means of a releasable retainer with the distal surfaces that comprise the tip of the instrument thus maintained in alignment. During insertion, the urethra is viewed by the healthcare worker throughout all or part of the insertion procedure by means of the viewer for the purpose of observing and identifying obstructions that may be present. Following insertion, the cable is withdrawn while allowing the catheter to remain in place within the urethra.

Another aspect of the invention is concerned with a surgical instrument, comprising a working sheath and obturator as well as a method for facilitating endoscopic examination and surgical procedures using such an instrument. The sheath is an elongated self-supporting tube with a lumen of sufficient size to accommodate other surgical instruments. During use, the instrument is placed into the body percutaneously or through a body passage into a body cavity, e.g., endoscopically through the urethra, trachea, esophagus or rectum, or into the peritoneal cavity. A removable obturator provided in the lumen to facilitate insertion of the sheath into the body. Once inserted, the obturator can be removed. Following this, the sheath is not moved while the operation is being performed. An inflatable balloon is preferably provided on the distal end of the sheath to hold it in place and thereby prevent retrograde movement. A peripheral duct or channel is also preferably provided for introducing lubricants during insertion or anesthetic during the procedure. While the working sheath remains in the body, any of various instruments selected by the surgeon, including instruments that are larger than the lumen of the sheath, can be inserted and removed by being passed into the body through the lumen of the sheath while the sheath remains in a substantially fixed position, i.e., stationary. The sheath thus acts as an artificial protective lining for the body opening through which it is passed, e.g., the urethra, gastrointestinal tract, bronchial tract, or percutaneous opening. The sheath can be used to introduce anesthetic and optionally lubricants to reduce discomfort or pain during insertion. In addition, the sheath can be used, if desired, to locate the distal end of any of a series of surgical instruments at a selected stop point with respect to the position taken by a preceding instrument. This feature may be very helpful with procedures under fluoroscopic (x-ray) guidance.

The invention thus provides a working sheath which can be thought of as a temporary and removable artificial tract or liner that is placed through an opening in the body of the patient at the beginning of a surgical procedure to facilitate endoscopic evaluation and treatment of the urinary tract or other body cavity for minimizing trauma and patient pain. During use, it allows multiple insertions and removals, i.e., the interchange of endoscopic instruments, catheters, drains, etc. At its proximal, i.e. exterior end, the lumen of the sheath has an entry port for instruments with a removable cap that provides a nipple seal to preclude backflow of fluid from the body after the obturator has been removed. The instrument can be placed into the urethra blindly with an obturator in the lumen or under direct vision, i.e., with a fiber-optic scope extending through the sheath to act as an obturator. In other words, the obturator itself can comprise a fiber-optic bundle for illuminating and viewing a body cavity through the sheath, both during the insertion of the sheath and thereafter.

THE FIGURES

FIG. 1 is a plan view of an instrument in accordance with the invention.

FIG. 2 is a longitudinal cross-sectional view of the instrument on a larger scale as it appears when inserted into a body cavity, in this case through the urethra into the bladder.

FIG. 2A is a view similar to FIG. 2 with the obturator removed.

FIG. 3 is a partial vertical longitudinal sectional view of the proximal end of the instrument in a sealed condition.

FIG. 4 is a vertical cross-sectional view taken on line 4—4 of FIG. 2A

FIG. 5 is a partial perspective view on a larger scale showing a portion of the instrument in accordance with the invention.

FIG. 6 is a perspective view of the proximal end of the invention showing the insertion of an endoscope through the lumen thereof.

FIG. 12 is an enlarged side elevational view of the invention partly in section with the tip of the fiberoptic viewing cable in position for insertion into the urethra.

FIG. 13 is a view similar to FIG. 12 showing the fiberoptic viewing cable with the tip in a retracted position.

DETAILED DESCRIPTION OF THE INVENTION

Figure 7:
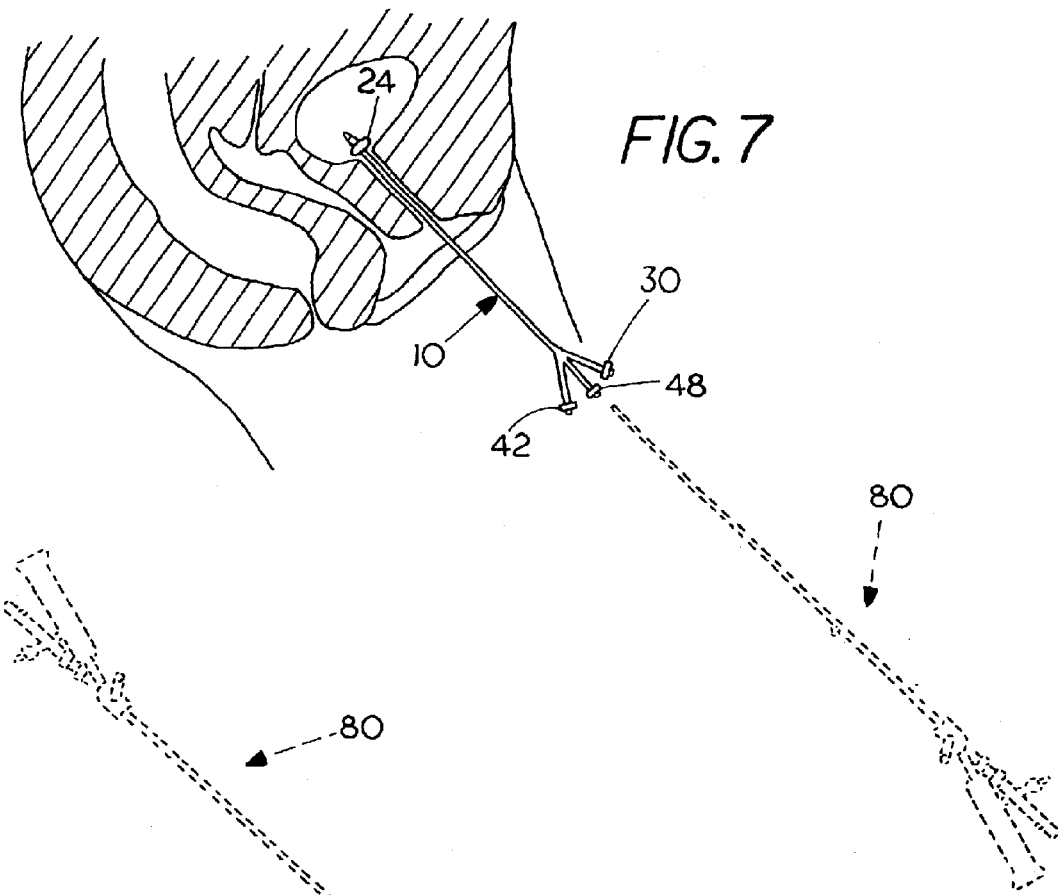
FIG. 7 shows the instrument in place within the female urethra.
Figure 8:
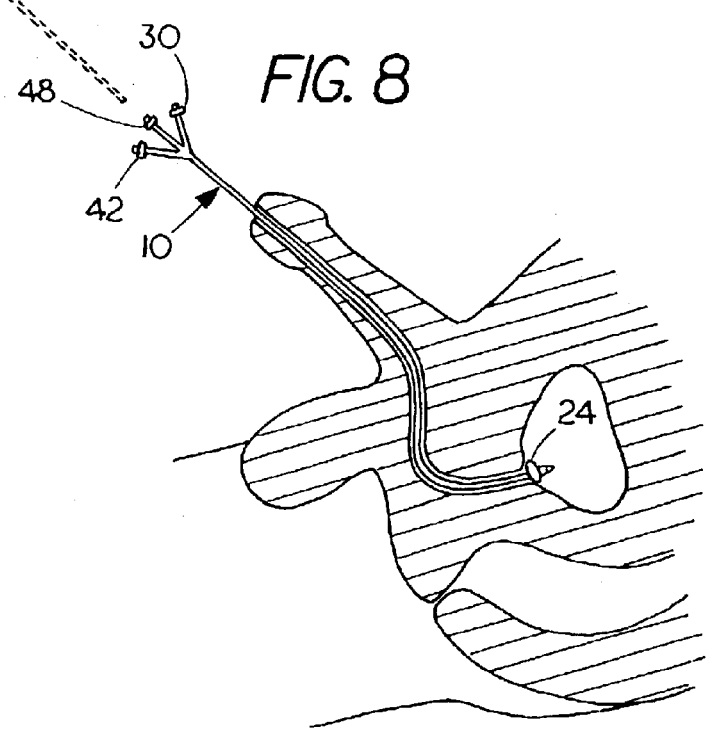
FIG. 8 shows the instrument positioned in the male urethra.

As mentioned briefly above, the working sheath of the present invention can be thought of as a temporary and removable artificial tract device or liner that is placed percutaneously or transurethrally to facilitate endoscopic evaluation and/or treatment of the urinary tract and other body cavities by enabling other surgical instruments to be passed through it into the body so as to minimize tissue trauma, discomfort or pain. Typically the sheath is about 40 cm long and has a central lumen that is typically about 6 MM (18 French) to 10 MM (30 French) in diameter. An inflatable circumferentially extending balloon is provided at its distal end. At the proximal end of the sheath are two tubular extensions for introducing fluid through longitudinally extending peripheral ducts or channels to be described in detail below. One channel is used for expanding a balloon to retain the sheath in place in the body. The second channel is used for introducing an anesthetic, medication or lubricant. The sheath preferably has a smooth finish with a low coefficient of friction. Optionally, a low friction coating can be provided to facilitate placement of the sheath within the body. The sheath can be formed from any of various well-known commercially available polymeric materials and can be either a Silicone or latex rubber, polypropylene or polyphylenene is preferred. When the sheath is formed from highly flexible material, a relatively stiff obturator is placed within the sheath to facilitate insertion of the sheath into the body. The sheath is inserted only once at the beginning of a procedure and therefore can be thought of as a single insertion instrument.

Refer now to the figures, and particularly to FIGS. 1–5.

As shown in the figures, the sheath, indicated generally by the numeral 10, has an elongated body portion 12 with a distal end 14 and an a proximal end 16. Inside the sheath 10 is a lumen or working channel 18 that extends the entire length of the sheath 10 and is provided with a distal opening 20 at one end and a proximal opening 22 at the opposite end. It will be noted that the distal end 14 of the sheath 10 adjacent the opening 20 is tapered at 21 so that its outer diameter is progressively reduced proceeding toward the opening 20. The sheath 10 can vary in length to suit the application to which it is applied, but in general it is typically from 30 cm to 50 cm in length and is preferably about 40 cm in length when it is to be used for gynecological procedures. It can be longer, say, 50 cm in length, when used in the male, for example, in a transurethral resection of a bladder tumor. For transurethral use, the outside diameter is typically about 9 mm (27 French) and the inside diameter about 5 mm (15 French). It should be understood that the dimensions presented herein are merely typical and can be varied to suit the circumstances in which the instrument is used.

At the distal end 14 of the sheath 10, which can be coated with a hydrophilic lubricant to reduce frictional drag during insertion, is provided an inflatable circumferentially extending annular balloon 24 formed from a ring of resilient elastomeric material such as synthetic rubber, latex rubber or the like, that extends around the sheath 10 adjacent the distal opening 20. It will be noted in FIG. 4 that the balloon 24 does not extend entirely around the sheath 10 but is provided with ends 24a and 24b that give the balloon 24a C-shaped configuration (FIG. 4) for purposes to be described below. Inflation air or liquid is supplied to the balloon 24 when required through a tubular extension 26 at the proximal end 16 of the sheath 10. If the sheath 10 is formed from an elastomer such as rubber, the balloon 24 can be integral with the sheath. However, if the sheath 10 is formed from a firm plastic material such as polypropylene, the balloon 24 is formed from rubber that is bonded to the outside surface of the sheath 10, i.e., by means of a suitable adhesive. The proximal extension 26 has a central passage 28 for inflation air or liquid which communicates with a longitudinally extending peripheral channel 29 that has a distal opening 3 communicating with the interior of the balloon 24. The free end of the tubular extension 26 is provided with an inflation port that preferably includes a Luer lock 30 through which inflation fluid (gas or liquid) can be introduced and retained until the Luer lock is opened.

The proximal end 16 of the sheath 10 has a second tubular inlet comprising an extension 32 with a central passage 34 that communicates through a longitudinally extending peripheral duct 36 with an opening 38 located a short distance, e.g., 1 or 2 cm, proximal of the balloon 24. The passage 34 terminates at its free end in an opening 40 that is sealed, e.g., by means of Luer lock 42. During use, an anesthetic, lubricant or other fluid can be introduced through the inlet 40 into the passage 34, the duct 36 and exits through opening 38 into the urethra, a portion of which is shown at 44 adjacent to the urinary bladder 46. The anesthetic or lubricant introduced in this way during placement in the urethra 44 will allow the sheath 10 to slide easily through the urethra 44 and will reduce patient discomfort. Endoscopic procedures thus can be performed with topical anesthesia supplied through the opening 38, with minimal sedation or light general or spinal anesthesia.

An advantageous feature of the invention is that the topical anesthetic or medication supplied through the opening 38, FIG. 2, is retained between the tissue and the sheath 10, thus preventing flushing so as to provide longer retention, tissue contact and effectiveness. Although the initial discomfort or pain will usually require topical or general anesthesia at the time of initial placement, the pain will become attenuated as a result the opening 38 as described. The instillation of the topical anesthetic can be administered intermittently as necessary through the delivery port 38 distal to the retention balloon 24. For example, lidocaine or other topical anesthetic solution or gel that is used for patient comfort can be diffused into the urethra lumen as the working sheath 10 is inserted. This holds or locks the medication between the urethral inner wall and the outer wall of the sheath 10 which will not absorb or allow the medication to flush or drop out, thus considerably concentrating and prolonging its effective pharmakinetic life. At the proximal end 16 of the sheath 10 is a circumferentially extending digital grasp ring or sleeve 48 which can, if desired, be provided with a non-slip knurled or other suitable high friction surface to make the grasp ring easy to hold onto as the sheath 10 is being manipulated. The ring 48 is preferably bonded to the sheath 10 by means of a suitable adhesive but, if desired, can be integral with the sheath 10. The tubular extension 32 can be used for any of a variety of purposes including, but not limited to, lavage, aspiration, irrigation, the introduction of medication such as an anesthetic, lubricant or antibiotic, or for other purposes. The extensions 26 and 32 are preferably about 120° apart when the sheath 10 is viewed from one end.

In the lumen 18 of the sheath 10 (FIGS. 1 and 2) is placed an elongated generally cylindrical obturator 50 having a parabolic insertion tip 52 at its distal end and optionally an enlarged head 54 at its proximal end, which functions as a handle to enable the obturator 50 to be easily inserted and removed from the lumen 18 of the sheath 10. It can be seen that the tapered portion 21 of the sheath 10 and the parabolic insertion tip 52 of the obturator 50 form a smoothly contoured surface that facilitates introduction of the instrument into the body, for example during a transurethral insertion through the urethra 44 into the bladder 46.

Refer now to FIG. 2 which illustrates a preferred form of obturator 50 in accordance with the present invention. Although the obturator 50 can be solid, in one form it comprises a stiff-walled tube having an interior 60 that is filled with internal supporting elements such as inert glass, metal or plastic beads 62. The beads 62 will enable the obturator 50 to flex at right angles to its longitudinal axis but will reliably prevent the obturator 50, as well as the sheath 10, from collapsing. In this way sufficient stiffness is assured so that the entire instrument consisting of the sheath 10 with the obturator 50 in place (FIGS. 1 and 2) within the lumen 18 can be inserted without difficulty through a body opening such as the urethra 44 without buckling, a problem sometimes referred to as a "wet noodle" effect wherein the article being inserted buckles as axial force is applied from its outer end during the insertion process. Typically, the obturator 50 has an internal diameter of about 4 mm and the beads can have it diameter of about 2 mm. The obturator 50 is typically formed from a plastic resin such as a polyolefin, e.g. polyethylene plastic. A head 54 has an extension 54a cemented inside the free end of the interior 60 of the obturator 50. Similarly, the insertion tip 52 is provided with an axial cylindrical extension 52a which is cemented within the hollow interior 60 of the obturator 50. Following insertion of the instrument into the body, e.g., through the urethra 44, the obturator 50 can be removed. As soon as this is done, the opening 22 at the proximal end of the sheath 10 can be sealed with a removable cap 70 formed from rubber or other suitable material with a central cylindrically-shaped, optionally barbed axial extension 72 that serves as a plug or nipple seal to prevent the loss of fluid from the body.

In another form, the beads 62 are replaced with a fiber-optic bundle 63 (FIG. 2) extending longitudinally the entire length of the obturator 50 and the insertion tip 52 comprises an optical lens for viewing and illuminating a body cavity or passage during insertion of the sheath containing the obturator, as well as after insertion.

Placed transurethrally, the invention permits accessing the entire lower and upper urinary tract by endoscopic instrumentation and offers the operator a spectrum of diagnostic or therapeutic options on preferred procedures. When placed percutaneously or through other body orifices, e.g., the trachea, esophagus or rectum, into other body cavities, it offers the same options. It allows multiple interchange of endoscopic instruments, catheters, drains, etc.

Figure 9:
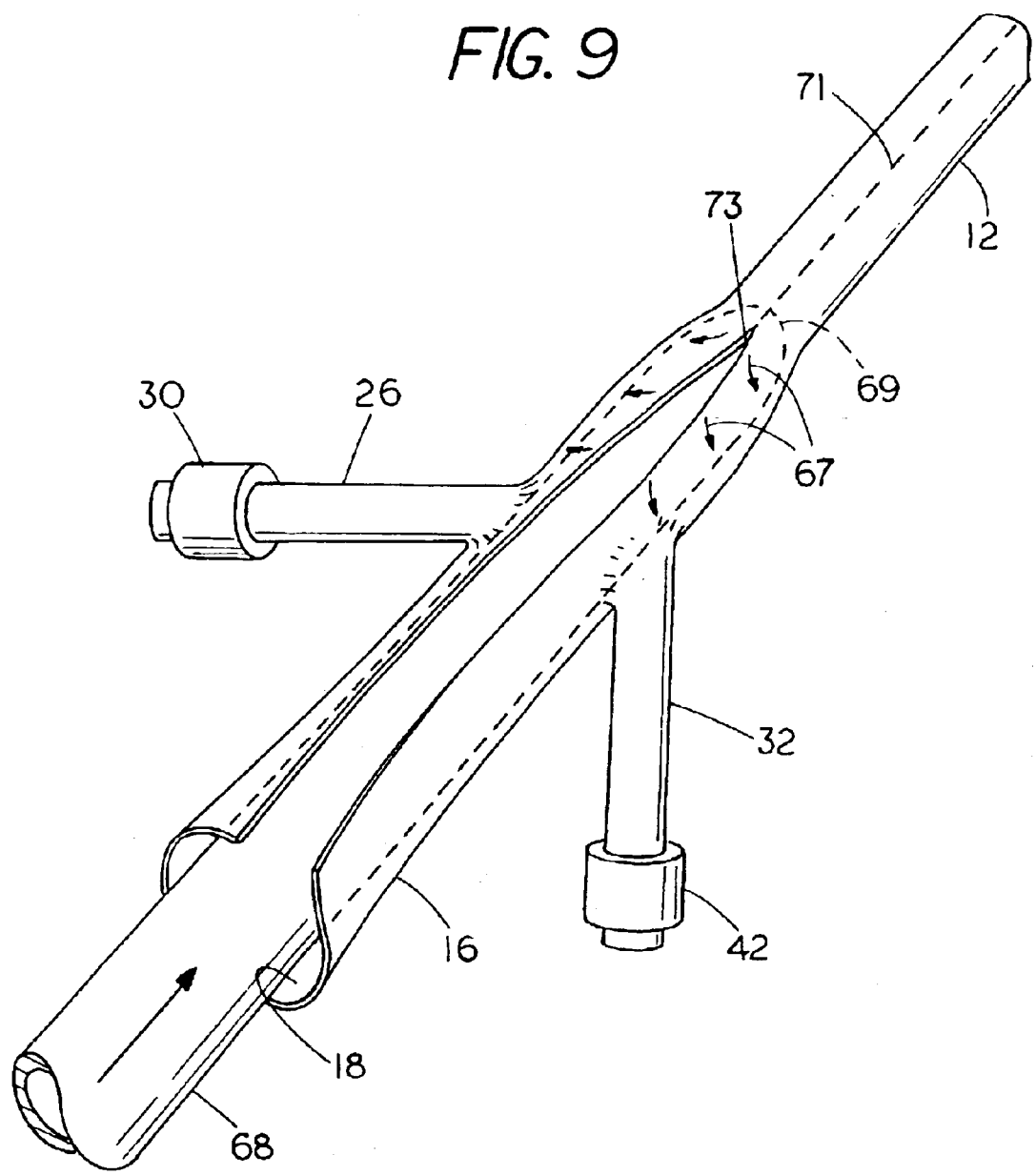
FIG. 9 is a partial perspective view of an optional form of the instrument that is adapted to split open along a separation line during use.

Under certain circumstances it may be necessary to insert a surgical instrument, e.g., 68 as shown in FIG. 9, of a larger diameter than can be accommodated by the lumen 18 of the sheath 10. The present invention provides a feature that facilitates the insertion of such an instrument. Refer now to FIGS. 4, 5 and 9. As shown in these figures, the sheath 10 is provided with a longitudinally extending line of weakness which serves as a separation line 71 along which the sheath 10 can split open as shown at 73 (FIG. 9). Thus, when the oversized instrument 68 is inserted, the pressure produced by the tip 69 of the instrument 68 will be directed circumferentially as indicated by the arrows 67 of FIG. 9. This stress will then split the wall 12 of sheath 10 open along the separation line 71 progressively proceeding toward the distal end 14 of the sheath 10 as the oversized instrument 68 is moved toward the right in FIG. 9. The separation line 71 can be provided by molding aligned longitudinally extending V-shaped indentations 74 and 76 into the wall 12 of the sheath 10 or, if desired, only a single indentation 76 can be used. Alternatively, when the sheath 10 is formed from an extruded plastic tube having an axial molecular orientation, no indentation 74 or 76 is needed. In that case, a tear can be initiated at a starting notch or slit 77 provided at 73 in the open end 22 (FIG. 2) and, once the ring 48 has been removed, the sheath 10 will continue to split open axially as the oversized instrument 68 is forced into the sheath 10. When the splitting at 73 is initiated, a low coefficient of friction on the mating surfaces is desirable so that the force is exerted to split the sheath 10 without causing excessive frictional drag. After the entire sheath 10 is split open, the balloon 24 is deflated as the seal with the sheath wall 12 is eliminated. The edges of the sheath 10 where it is split apart must not be sharp and therefore will not macerate the lining of the urethra 44 during withdrawal. The unique splitting open or unzip feature provided by the separation line 71 already described, which is preferably situated midway between the extensions 26 and 32, allows placement of an oversized instrument, catheter or other device of greater outside diameter than the lumen 18 of the sheath 10. The unzip feature of the instrument is activated and initiates a splitting of the working sheath 10 as the oversized instrument, drain, catheter or other device 68 is inserted, thus opening the working sheath 10 completely.

Refer now to FIG. 6 which illustrates how the working sheath 10, after placement in the urinary tract via the urethra, male or female as the case may be, facilitates the insertion of an endoscopic or fiber-optic instrument 80 of known commercially available construction with an optic linkage 82 via camera 85 to a light source 84 for projection to make possible the inspection and visible exploration of the entire urinary tract or other body cavity via percutaneous entry. If desired, the obturator 50 containing the fiber-optic bundle 63 (FIG. 2) can be optically connected at its proximal end with the distal end 81 of the fiber-optic instrument 80 of FIG. 6 so that illumination and viewing of a body passage or cavity can be carried out through the obturator 50.

The invention has numerous benefits and advantages. It offers a passive assistance to the operating physician. For example, in urology during endoscopic procedures, placement in the urethra provides additional patient safety, reduced tissue trauma, increased comfort and speed during the procedure with minimal tissue irritation. It thus offers reduced healing time and iatrogenic infection potential. Moreover, the instrument of the present invention can be made disposable, as well as being readily placed and retained in the male or female urethra during use and is subsequently easily removed upon procedure completion for discard when in a disposable form. The instrument can be fabricated from any suitable biocompatible polymeric material in compliance with CDRH as well as FDA standards and specifications. It can be easily mastered for efficient use, as minimal training would be indicated.

The obturator 50 can be employed as described hereinabove or, if desired, the obturator 50 can comprise a commercially available endoscope of suitable known construction which will then serve as an obturator during placement of the working sheath 10 in the urethra or other body or surgical opening in the body. The invention can also be used to access gastrointestinal or pulmonary tracts or percutaneously into any body cavity.

The invention provides numerous endoscopic instrument choices: cystoscope, ureteroscope, future specialized urological endoscopes, electro-cautery delivery, light and laser light delivery, and the like. The obturator 50 can be configured for conformation to male or female urethra multiple angulations, i.e., can be curved as desired. In addition, the invention is applicable in multiple medical specialties including urology, gynecology, general surgery, vascular surgery, gastroenterology and pulmonary medicine, radiation treatment, etc. Since the invention provides a large working sheath for lavage capability or instrumentation in the sheath 10 itself, the fiber-optics that are inserted through the lumen 18 offer better visualization to the operator. The Luer locks 30 and 42 limit instrument position shifting and back flushing. In addition, larger and/or rigid instruments can be easily passed through the working sheath 10 without trauma to the urethral tissue, thus offering greatly improved patient comfort.

Endoscopic and percutaneous procedures prior to the present invention frequently required time consuming insertion and removal of instrumentation which commonly caused tissue trauma, discomfort and pain as the instrument was passed to the surgical site. General anesthesia was frequently necessary because of the discomfort and pain associated with these procedures. The invention inherently makes many of these issues moot. Also, as a result of the above benefits, the invention reduces the risk of iatrogenic infection, bacteremia and/or potential sepsis common with the trauma associated with the insertion and removal of multiple instruments endoscopically or percutaneously. Once placed in the urethra, the sheath prevents scarring and maceration of urethral tissue when multiple procedures and instruments are passed. This saves a substantial amount of time for the physician and reduces patient discomfort or pain. The invention can be adapted to access the upper urinary tract for efficient diagnosis, identification and manipulation of bladder and kidney stones of various types with minimal discomfort to the patient. Bladder stones and other foreign objects can be rapidly removed without tearing the urethral mucosa. The invention also facilitates more office or outpatient surgery as it minimizes the need for general anesthesia.

The invention is also useful in laparoscopic bladder suspension procedures so that the operator can identify the bladder wall for suture or staple placement. The cystoscope operator can direct light on the internal bladder wall and extract a staple or suture through the urethral exit route using the invention. Moreover, the invention has a channel 36 built in that can be used with a negative pressure for aspiration of laser or electrocautery smoke or vapor through a filter and trap system external to the urethra. The negative pressure port 36 for laser smoke or vapor removal passes into a filter trap disposal system (not shown), which is readily available.

The invention also facilitates the withdrawal of debris such as bladder or kidney stones which can be removed in larger fragments or by irrigation after being crushed mechanically or by lithotriphy (sonically, laser or electrohydraulic energy), either by aspiration through the lumen 18 or through a catheter (not shown) that is placed within the lumen 18. In this way debris can be removed without anesthesia or pain and with minimal tissue trauma using a rubber catheter (not shown) placed within the sheath 10. Less postoperative pain, faster healing, discharge of medication and endothelial cells or urine is assured.

Briefly, in removing kidney stones, the procedure is commenced with the working sheath 10 in place in the urethra. If desired, the unzip option is invoked to place a larger diameter catheter 68 within the sheath 10. Ureteroscopy can be done with a ureteroscope which can be rigid or flexible through the working sheath 10 surrounding the instrument substantially reduces patient discomfort and length of the procedure.

The instrument according to the invention is delivered to the physician in a sealed package (not shown) with the obturator 50 in place within the lumen 18 of the working sheath 10. At this point the obturator 50 can be removed and replaced with a cystoscope or other suitable instrument that serves as an obturator for insertion if the operator so chooses. Insertion, either by the obturator 50 or the cystoscope 80 is made until the inflation balloon 24 clears the opening of the bladder 46. This can be determined by reading the depth of the insertion lines (not shown) that are printed on the sheath 10 at the urethral entry point. A lubricant and anesthetic gel or fluid should be employed in the urethra to facilitate placement with minimum pain. Upon inflation of the balloon 24 through the duct 29 with gas or fluid, a slight retracting pull should be made to assure that the bladder wall has retained the sheath 10. The check valve in the Luer lock 30 will maintain the pressure to keep the balloon 24 inflated. The obturator 50 then can be withdrawn and a cystoscope 80 placed within the sheath 10 to view the inside of the bladder 46. This is accomplished by grasping the proximal end 16 of the sheath 10 with the left forefinger and thumb by means of the grasp ring 48 and retracting the obturator 50 with the other hand. The obturator 50 will have served its role to insert the sheath 10 through the many curves of the urethra 44 into the bladder 46. The working sheath 10 is now in place so as to permit therapeutic treatment or diagnostic perspective for the operator. The instillation ducts 34, 36 can deliver solutions, e.g., lidocaine for numbing the tissue, medication, etc., and an endoscopic device 80 can be introduced to deliver light, e.g., laser energy for viewing or desired treatment (laser, cryonic, pyronic, electrocautery) and the like.

During laparoscopic surgery, in the space of Ritzius (the preperitoneal cavity), it can be to the patient's and surgeon's advantage (with respect to visual positive identification orientation minimization of urinary tract infections and contamination, the time required for reinsertion of a cystoscope, etc.) to have rapid access to an internal view of the bladder itself, and this is readily accomplished through the use of the present invention. Staple and suture penetration of the bladder wall is visually apparent and a urethral catheter or stent can be inserted through the sheath 10. The light provided by an endoscope can be used to transilluminate and delineate the bladder or bladder wall during laparoscopy. Enlargements, wall thickening, vessel enrichment, which all may herald benign or malignant growth, should be more apparent to the operator using the invention. The invention also facilitates the disposal of urine from the bladder that is generated during the procedure. One primary advantage of the invention is to permit rapid insertion and removal of the cystoscope 80 or other useful instrument during endoscopic operative procedures while minimizing the time required to complete the operation while reducing cross-contamination and infection generation, all of which are very advantageous to the patient by ensuring safety while minimizing the time during which the patient is at risk.

EXAMPLES

Typical methods of using the instrument in accordance with the invention will now be described by way of example.

Example 1

The use of the instrument in accordance with the present invention will be described in carrying out a transurethral resection of a bladder tumor. This procedure is usually performed under a general or spinal anesthetic because of the discomfort/pain from passage of the instrument and also from that which might occur from the resection of the tumor by electrical current. However, if one is using laser energy (neodinium YAG or Holmium lasers, for example), the patient's intraoperative discomfort/pain is usually less as these procedures can, in that case, be performed without general or spinal anesthesia.

First, the working sheath 10 is inserted through the urethra as shown in FIG. 2. The obturator 50 is then removed. Generally, a rigid cystoscope (usually 20–23 French) is passed through the lumen 18 of the sheath 10 with a rigid optical lens to evaluate the urethra and bladder to determine the number of tumors, their locations, extent of involvement of the bladder, and possible involvement of ureteral orifices (where the ureters enter into the bladder). After the endoscopic assessment is performed with the rigid scope, it is removed and the biopsy instrument can be passed through the lumen 18 of the instrument 10 to obtain small biopsies of the tumor and other locations in the bladder. At this point, to treat the tumors by resection (usually electrocautery), the entire rigid cystoscope and scope is removed from the lumen 18 while the instrument 10 remains in place so that a larger instrument (resectoscope) can be passed through the lumen 18. It is not uncommon that, prior to the passage of this larger instrument, it will be necessary to dilate the urethra with a series of instruments called 'sounds' to at least 28 French or larger depending on the size of the resectoscope chosen (and this is based generally on the size of the tumor to be resected).

The resectoscope is passed through the lumen 18 of the sheath 10, either blindly with its own obturator in place therein or under direct vision with a rigid fiber-optic scope in place. The resection of the tumor or tumors is then undertaken. Eventually, the tumor fragments will have to be removed. The tumor fragments may be removed during the procedure if necessary, or at the end of the procedure.

Once a satisfactory resection and removal of tumor fragments has been accomplished, it is necessary to remove the rigid resectoscope from the lumen 18 and pass a catheter through the lumen 18 for temporary irrigation and drainage of the bladder or leave the sheath 10 in place and hook up to a drainage bag for irrigation. Continuous postoperative irrigation may be necessary, as inevitably there will be bleeding after the procedure. If the blood is not irrigated out, clots will form which will result in obstruction of the catheter or, if the catheter has not been left in the urethra, resulting in urinary retention. On occasion, bleeding can be so extensive that clot formation cannot be prevented despite irrigation. In these situations, the patient is usually taken back to the operating room on an emergency basis and given another general anesthetic so the patient will not experience severe pain upon reinsertion of instrumentation such as a resectoscope.

Some of the primary advantages of the invention are the following. First, depending on the size of the tumor, the entire procedure may be accomplished under local anesthetic and limited sedation because manipulation of the lower urinary tract would be limited to the initial passage of the working sheath 10. This would be quite similar to the office cystoscopy which requires generally only topical anesthesia (lidocaine jelly instilled into the urethra). Second, tissue trauma or injury which can cause bleeding or scarring is minimized because there would be no repeated trauma to the urethral mucosa lining. Third, if it is necessary to pass a larger catheter for irrigation and drainage at the end of the procedure, this can be done without significant discomfort or trauma because of the unzip feature of the sheath 10 which allows it to split at 73 along line 71. Fourth, postoperative bleeding, which may necessitate a return to the operating room, may be handled on the floor or, if necessary, in the operating room without an anesthetic, as an armamentarium of available endoscopic instruments could be passed through this working sheath 10. Fifth, the overall procedure should be less time consuming because of the rapidity with which instrumentation can be passed through the working sheath 10. This assures safe passage of instrumentation to the operative site (bladder) and reduced risk of false passage into the urethra which can occur upon multiple passage of instrumentation transurethrally. Finally, economic savings can be realized because of less time in the operating room, less or lack of anesthesia, surgeon's time, and disposable instrumentation.

Example 2

The invention will now be described in conducting a laparoscopic pelvic reconstruction procedure, e.g., culposuspension, paravaginal repairs, and enterocele repairs.

First, the working sheath 10 is inserted as shown in FIG. 2. The obturator 50 is then removed. A Foley catheter is then passed through the lumen 18 of the sheath 10 to keep the bladder empty, or the sheath 10 itself can be used for this purpose without a Foley. When the procedure is performed laparoscopically through the working sheath 10, it is frequently necessary to perform a cystoscopic evaluation with the examination of the bladder by passing urethral catheters through the lumen 18 (performed cystoscopically) during or at the end of the laparoscopic procedure. The Foley catheter is removed and the cystoscope is introduced next through the lumen 18 of the sheath 10.

If it is necessary to perform the evaluation during the laparoscopic procedure, it is necessary that the surgeon carry out the procedure from the operative site on the abdomen to between the patient's legs and remove a Foley catheter that was placed in the sheath 10 at the beginning of the procedure to keep the bladder empty, therefore minimizing injury rate during the laparoscopic exposure and dissection necessary to perform the above reconstructive procedures. After the Foley has been removed, the surgeon must then pass a rigid cystoscope through the lumen 18 of the sheath 10 to inspect the bladder or to pass ureteral catheters.

The advantages are many if one is able to use the working sheath 10. First, transurethral diagnostic and endoscopic procedures are performed without having to remove the sheath 10 which was placed at the beginning of the procedure for bladder drainage. This by itself would decrease intraoperative time. Second, having the surgeon leave the intra-abdominal operative site to take a position below is avoided. He can simply pass the flexible scope through the lumen 18 of the working sheath 10 to inspect the bladder via CRT or directly through a lens and possibly even define the bladder transurethrally which is frequently helpful when performing a laparoscopic procedure. Third, even ureteral catheterization could be performed. Actually, the working sheath 10 gives the surgeon the option of not even having to place the patient in the dorsal lithotomy position for these procedures if a flexible scope or instrumentation is used. The procedure described also potentially decreases the risk of intraoperative iatrogenic infections and concretely procedure times.

Example 3

The invention will be described in removing kidney stones, Nephrolithiasis (renal and ureteral calculi) are quite common urologic problems, requiring emergent surgical intervention. When renal or ureteral calculi are causing blockage of the upper urinary tracts, patients will most commonly experience severe and disabling colicky pain requiring immediate emergency medical attention, including pain management and surgical intervention. No population is immune from the renal colic attack as a result of kidney stones (and as will be discussed later), especially astronauts who are at even greater risk. When these attacks occur, patients are initially evaluated in the emergency room. Once the diagnosis of nephrolithiasis is made, they are admitted to the hospital for management and probable surgical intervention if it is unlikely they will pass the stone on their own or if pain management is a problem.

First, the working sheath 10 is introduced into the bladder as shown in FIG. 2 and the obturator 50 is then removed. The surgical procedure will depend on the size and location of the stone along with complicating factors. If the stone is in the upper urinary tract (kidney or upper two-thirds ureter), it is possible to disintegrate the calculus by extra-corporeal shock wave lithotripsy. However, if the stone is causing high-grade obstruction of the ureter, it will be necessary to pass a ureteral stent through the lumen 18 of the instrument 10 to relieve the obstruction and also alleviate the pain. The stent is generally passed transurethrally through the lumen 18 after the patient has received a general anesthetic. This is accomplished by placing the patient in the dorsal-lithotomy position. A rigid cystoscope is then passed transurethrally through the sheath 10 into the bladder. Through the scope, the stent is then negotiated into the ureteral orifice and into the upper collecting system, bypassing the calculus.

Generally, the stent is positioned in the upper collecting system using fluoroscopic guidance. Fluoroscopy may not be necessary if one has an accurate pre-operative measurement of the ureter, which can be obtained from an excretory urogram. Sometimes, the surgeon may elect to extract the calculus rather than passing a stent, and this is done by removing the cystoscope and then inserting a ureteroscope. The ureteroscope is then negotiated through the ureteral orifice up into the ureter to the point where the calculus is visualized. A stone basket is passed through the operating channel of the ureteroscope and the calculus is extracted under ureteroscopic guidance. Because of the edema and inflammation from the calculus itself and manipulation of the calculus, the ureter will frequently obstruct and this will cause further pain to the patient. The most common way of addressing this problem is to place a ureteral stent after the calculus has been extracted.

The advantages of the working sheath 10 of the present invention are obvious. They include a possibility of performing this procedure without a general anesthetic, less operative time, and less chance for infection.

The invention can be used in treating a condition that is experienced by astronauts. The most common surgical emergency that has plagued astronauts has been the formation of nephrolithiasis as a result of being in a weightless environment. The weightless environment is quite similar to what is experienced by patients who are immobilized for long periods of time. Astronauts and patients who are immobilized experience calcium attrition and subsequent increased urinary excretion, of which can result in the formation of renal calculi. When astronauts experience renal colic, this is truly a grave situation as they are unable to perform their duties. With the increasing distance and duration of space missions and NASA's manning a space station, it is problematic to return astronauts to earth for emergency medical treatment. Since travel in space can lead to renal colic pain, whether here on earth or in space, the strongest parenteral pain medication (opiate) is required. These patients also experience severe nausea accompanying the pain. NASA is presently trying to come up with solutions to treat these episodes in the space station. Administration of general anesthetic in space is a great challenge as it requires someone skilled in anesthesia and because administering anesthesia and I.V. fluids in space is a difficult problem due to lack of gravitational force requiring specialized equipment and techniques. An important advantage of the present invention in this application is the potential for allowing treatment of these stones endoscopically without a general anesthetic.

Briefly, in accordance with another aspect of the invention (FIGS. 10–16), a flexible direct vision viewing instrument or viewer, e.g., having fiberoptic shaft or cable, is placed within a urinary catheter with its tip located at a distal end of the catheter so that the surfaces at the distal tip of both the viewing cable and the catheter are aligned, i.e., are flush, to fit together in such a way as to form a smoothly curved end surface for negotiating obstructions as easily as possible. The cable is maintained in this position within the catheter by means of a releasable retainer with the distal surfaces that comprise the tip of the instrument thus maintained in alignment. During insertion, the urethra is viewed by the healthcare worker throughout all or part of the insertion procedure by means of the viewer for the purpose of observing and identifying obstructions that may be present. Following insertion, the cable is withdrawn while allowing the catheter to remain in place within the urethra. Refer now particularly to FIGS. 10–15 which illustrate this embodiment of the invention wherein the same numerals designate corresponding components already described.

Figure 10:
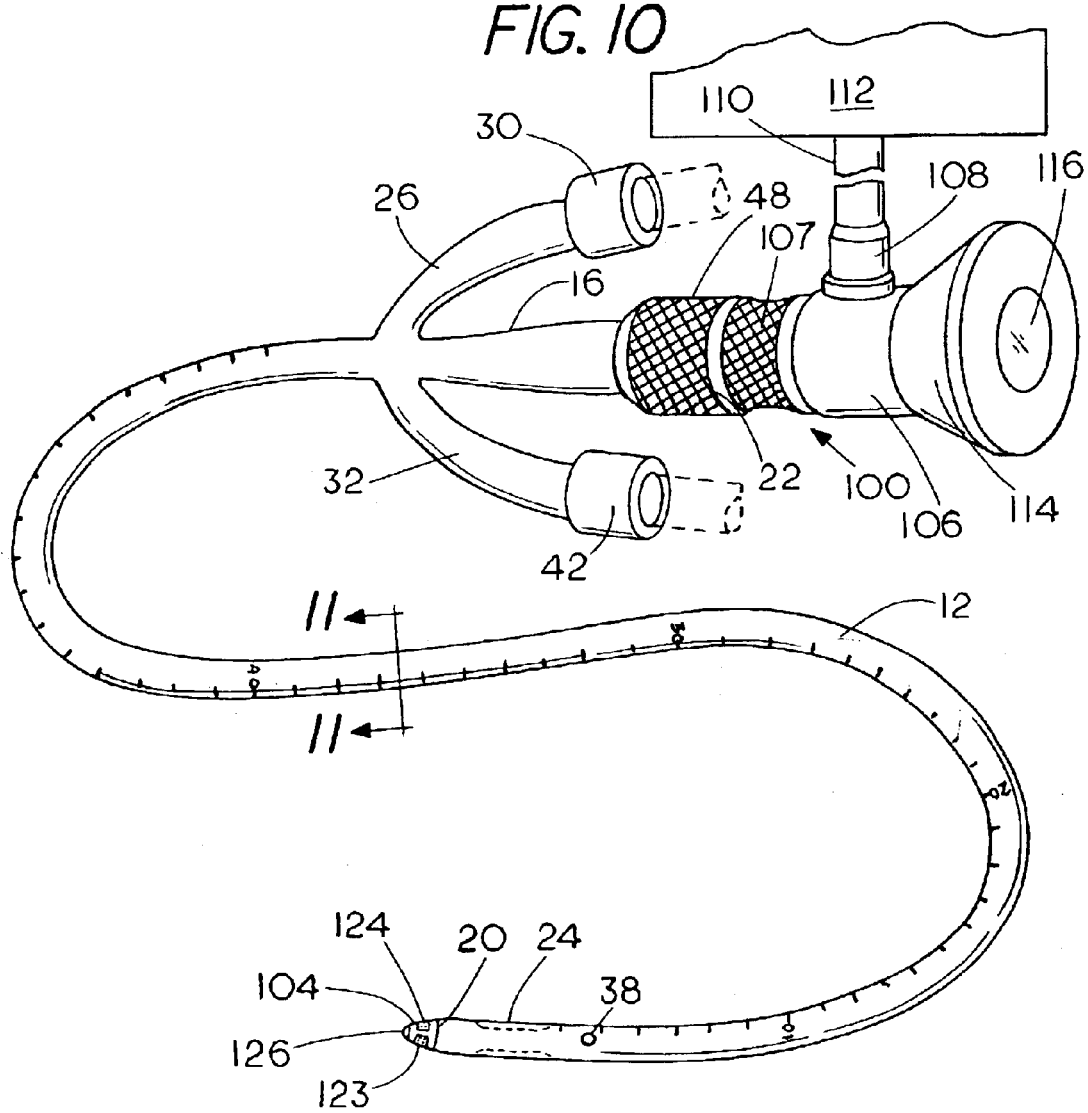
FIG. 10 is a perspective view of another form of the invention showing a fiberoptic viewing cable in place within a urinary catheter as it appears just prior to use.
Figure 11:
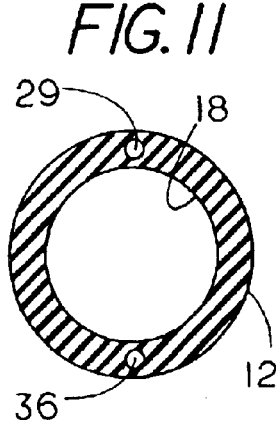
FIG. 11 is a vertical cross sectional view taken on line 11—11 of FIG. 10 on an enlarged scale with the cable removed.

In this embodiment of the invention, the obturator 50 is replaced by a flexible direct viewing instrument having a flexible fiberoptical shaft or cable. The viewing instrument or viewer indicated generally by numeral 100, has a cable or shaft portion 102 with a distal tip 104. The shaft 102 of the viewing cable can be made detachable from the viewing body 106 so that the viewing body and eyepiece can be used repeatedly while the plastic shaft 102 can be a single use item. However, if the entire optical system is constructed to be sterilized it can be supplied as a multi-use unit. As can be seen in the Figures, the tip 104 of the flexible cable 102 has a smoothly curved generally parabolic or rounded end surface. While no precise mathematical formula for the curvature of the tip 104 is necessary, it is important that the end of the tip be rounded or curved rather than having a sharp point. The end can be thought of as parabolic, bullet-shaped or dome-shaped. The numeral 12 in this embodiment represents a catheter rather than a sheath and can be structured generally much like a standard urinary catheter. The catheter can be from about 10–20 French (3–7 mm) but is preferably in the range of about 13–15 French (about 4–5 mm). The catheter 12 and shaft 102 of the instrument 100 is of a standard length, e.g., 50 cm for a male patient. The catheter 12 is provided with centimeter marks as shown in FIG. 10.

The catheter 12 has a distal opening 20 that is located centrally and in alignment with the longitudinal axis thereof. The outside surface of the catheter 12 adjacent to the opening is tapered at 21 to provide a smoothly curved contour that tapers centrally toward the distal tip of the instrument. In a preferred form of the invention, the shaping and positioning of the rounded cable tip 104 and the adjacent tapered contour 21 of the catheter 12 are related to one another while in the insertion position so that the curved distal end surfaces are aligned, i.e., flush, as clearly shown in FIGS. 10, 12 and 14 whereby, together, their surfaces form one substantially continuously curved composite tip surface that tapers centrally proceeding toward the distal end thereof with a blunt end to facilitate insertion into the urethra and aid in the negotiation of obstructions if any are encountered. It is thus the curvature of the tip of the cable that includes the viewing port and light supply together with the tapered end portion 21 of the catheter which cooperate to provide the smooth bullet-shaped or dome-shaped surface that helps the instrument move easily through the urethra, passing any obstructions that may be present.

As shown in FIGS. 10–13, the viewing instrument 100 includes the viewing body 106 that is provided with a fiberoptic light coupling 108 to which light is introduced from a fiberoptic feed cable 110 connected to a suitable light source 112 that can comprise any suitable light for illumination known to the art. A relatively inexpensive light source is preferably used, such as a battery-operated source, e.g., a combination of say a dozen light emitting diodes (not shown) that are optically coupled to focus light onto the input end of the feed cable 110. Other well-known light sources such as a 300-watt xenon lamp or other light source can be used but are more expensive. At the right end of the instrument 100 is an eyepiece 114 having a viewing lens 116 (FIG. 1). Next to the viewing body 106 is a handgrip 107.

As shown in FIGS. 12 and 13, the cable or shaft 102 is provided with a radially outwardly extending annular projection 116 which in this case is circular but can be of any shape desired and is sized to fit in either of two longitudinally spaced apart circular grooves 118 and 120 within the lumen 18 of catheter 12 to serve as a retainer for holding or locking the shaft 102 of the instrument in either an extended operating position of FIG. 12 or an alternate recessed viewing position shown in FIG. 13 in which the tip 104 is recessed slightly, e.g., 2 mm behind the opening 20 at the tip of the catheter 12 to provide enhanced viewing under certain circumstances, particularly when the urethra is collapsed or when an obstruction is encountered, and the viewing tip 104 is pressed tightly against the tissue of the body. Under these conditions, all that can be seen through the eyepiece 116 is a pink or red color. When this condition occurs, the operator need only withdraw the cable slightly from the operating position of FIG. 12 to the retracted position of FIG. 13 by pulling outwardly on the handgrip 107. The groove 120 acts to securely hold the tip 104 in a slightly retracted position so that the surrounding tissue can be more clearly seen. Clear saline can also be introduced through the duct 36 for washing away any blood or debris or to slightly distend the urethra if desired. Thus, the enlargement 116 and the cooperating recesses 118 and 120 in the catheter serve as a simple and reliable retainer for releasably holding the viewing tip 104 in the operating position of FIG. 13 in which the tip is aligned with the tapered portion at the end of the catheter to form one continuous, smoothly contoured surface to ease the instrument through the urethra or, if desired, to hold it in the retracted position of FIG. 13 for viewing when the tip would otherwise be in contact with the surface of the urethra or an obstruction. As soon as the obstruction has been viewed with the tip 104 retracted so that any difficulty can be more easily observed and understood, the tip can be returned to the position in FIG. 12 and the insertion process continued, the smooth surface at the tip 104 enabling any obstruction to be passed as easily as possible.

Figure 14:
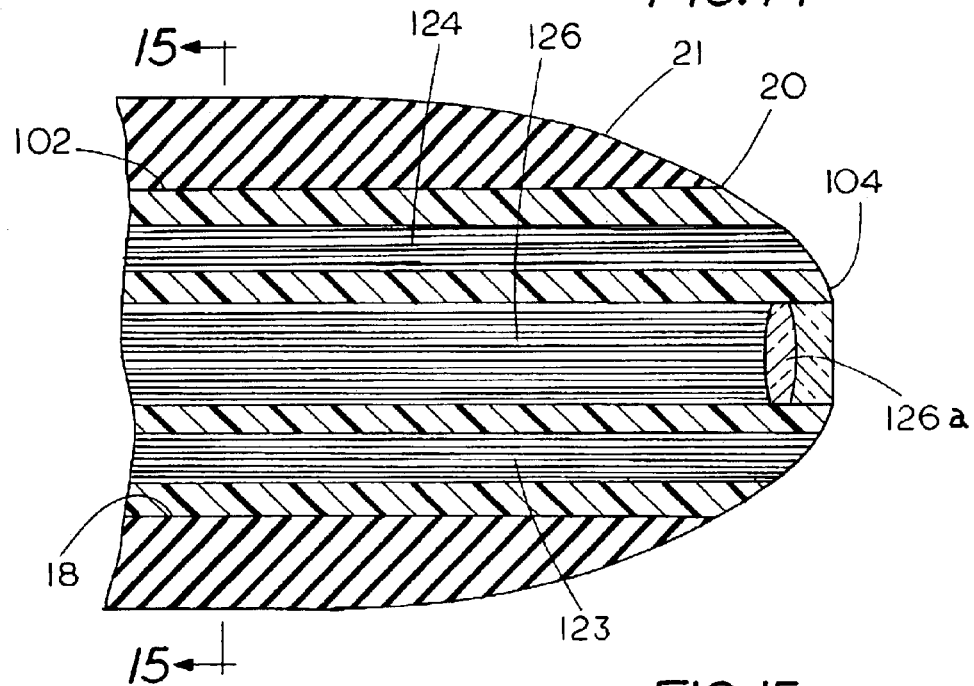
FIG. 14 is a vertical cross sectional view of the tip of the instrument with the fiberoptic viewing cable in the position taken during insertion into the urethra as shown in FIG. 12 but on an enlarged scale.
Figure 15:
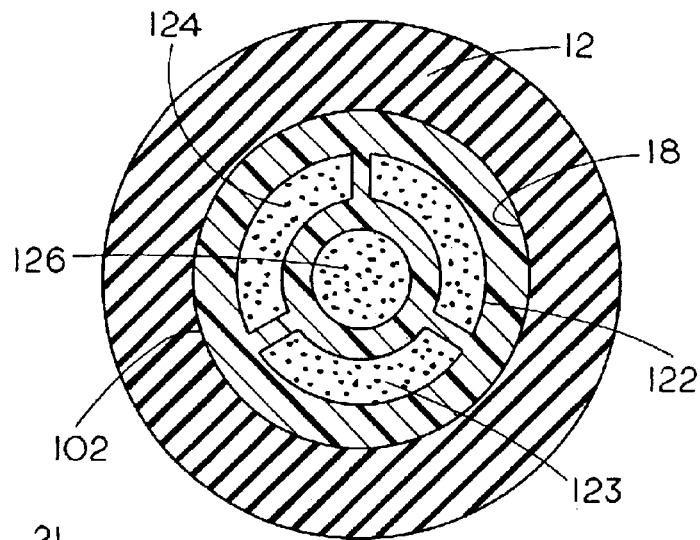
FIG. 15 is a vertical cross sectional view taken on line 15—15 of FIG. 14.

Refer now to FIGS. 14 and 15 which illustrate the internal structure of the shaft 102 and catheter 12 in more detail. As noted above, the shaft 102 of the viewing instrument 100 is slideably supported within the lumen 18 of the rubber catheter 12 and can be slid longitudinally therein when desired. A lubricant can be provided between the catheter 12 and the shaft 102 to allow it to slide more easily. Within the cable or shaft 102 the instruments are provided three flexible fiberoptical illumination bundles 122–124 for supplying light to illuminate the area in front of the distal tip 104 of the instrument and a centrally located flexible coherent fiberoptical bundle 126 for transmitting the image from the objective lens 126a at the distal tip of the shaft 102 to the eyepiece lens 116. The circular arrangement fiber bundles 122–124 of FIGS. 14 and 15 provide even distribution of light throughout the field of view. It will be noted that the opening 20 at the end of the catheter 12 is aligned centrally with the longitudinal axis of the catheter for allowing zero degree viewing, i.e., straight ahead, through the lens 120a.

Figure 16:
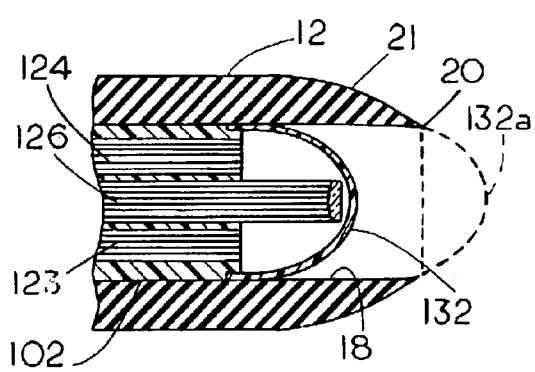
FIG. 16 is a vertical longitudinal sectional view of the distal end of another alternative fiberoptic viewing cable in accordance with a modified form of the invention as seen in the retracted position.

Another form of tip for the cable 102 is shown in FIG. 16. In this embodiment, the illumination fiberoptic bundles 122–124 are cut off straight to provide a flat end surface. The coherent viewing fibers 126, however, extend further distally. To provide a curved end surface for the flexible shaft 102, the end of the shaft is enclosed within a smoothly contoured, optically transparent plastic dome 132 as a part of the shaft that can be formed from any suitable transparent material, such as glass, but is preferably formed from transparent plastic resin having a refractive index approaching optical grade glass and covered on both surfaces with an antireflective coating. When the shaft 102 is extended distally to the operating position, the dome 132 will take the position shown by dotted lines 132a which cooperates with the tapered surface 20 of the catheter 12 so that the two surfaces join together to provide a single smooth and continuous generally bullet-shaped or dome-shaped surface that tapers centrally proceeding toward its free end to facilitate insertion to the greatest extent possible.

While not preferred, the invention also contemplates the possibility of provided steering cables, e.g., four steering cables within the shaft 102 for the purpose of turning the tip either from side to side, or up and down. This modification is not preferred because of the added cost.

The method of use of the apparatus described in FIGS. 10–16 will now be described. The catheter 12 and the illumination instrument 100 are packaged separately in sterile containers. Just prior to use, the containers are opened and the flexible shaft or cable 102 of the instrument 100 is inserted into the lumen 18 of the catheter 12 and releaseably retained in the position of FIG. 12 so that the distal tip of shaft 102 extends slightly through the opening 20 with the tapered surface 21 of the catheter aligned, i.e., flush, with the adjacent surface of the distal tip 104 of the instrument 100 so that the surfaces form a single continuous, smoothly contoured composite surface as described above.

The tip 104 is inserted into and advanced through the urethra. The lighting system 112 is energized so that light is transmitted through the feed cable 110 thence through the fiber bundles 122–124 (FIGS. 14 and 15) to illuminate the inside of the urethra. Light from the illuminated body tissue of the patient is then carried back from the objective lens 126a through the coherent fiber bundle 126 to the eyepiece 114 of the instrument allowing the healthcare worker, the physician's assistant, nurse, other healthcare provider or in some cases the patient to observe the urethra through the eyepiece lens 116 during insertion. As this is done, any obstructions that may be present can be observed through the lens system. In the event the tip 104 of the viewing cable becomes pressed up against the wall of the urethra or is for any other reason in contact with the surface of body tissue, the operator can then, by placing the fingers of one hand on the handgrip 107 and the other on the collar 48, withdraw the shaft 102 to the retracted position of FIG. 13 by sliding the projection 116 into the groove 120. When this is done, the open tip 20 of the catheter 12 will hold the body tissue surface a short distance away from the objective lens 126a allowing the adjacent surface of the body tissue to be more clearly seen. If an obstruction such as a stricture, stone or scar tissue is encountered, it can be seen by the operator, thus enabling the operator to know the general nature of the obstruction. Most of the time this will enable the user even though not a board certified urologist to continue with the insertion of the catheter and avoid iatrogenic trauma strictures, urethral bleeding, or other difficulties such as urethra mucosal lining tears, patient pain, scar tissue formation, or treatment delays as well as the increased costs that result. However, if the nature of the obstruction is not understood or if further difficulties are encountered, the operator will at least have some information available for a urologist who may have to finish the intubation. In addition, if the field of vision is obscured, saline can be introduced via passage 36 and opening 38 into the urethra for washing away debris in front of the objective lens to provide better visibility. The flexible viewing cable 102 also aids in the insertion of the catheter 12 by filling the lumen 18 so as to prevent the catheter from collapsing and as well as giving it a degree of stiffness. However, the catheter 12 can, if desired, be passed into the urethra without the viewing instrument 100 in place and the viewing instrument inserted later if an obstruction is encountered.

Once the catheter 12 has been inserted completely, fluid is introduced through the duct 29 causing the distal balloon 24 to inflate conventionally for holding the catheter in the bladder. The instrument 100 is then removed. While the main purpose for inserting the catheter 12 is for urinary drainage, it is also used to diagnose problems or maintain anatomic continuity.

Thus, the invention provides a method and apparatus for more efficiently and safely passing a urethral catheter into the bladder of a male or female human patient and is particularly beneficial in enabling obstructions to be observed directly during intubation. It is especially well suited for negotiating obstructions of any sort such as anomalous structures, scars due to injury or infection or stones, enlarged prostate due to cancer or AIDS or related tissue deterioration. A nurse, physician's assistant, resident or other healthcare worker is able, using the invention, to pass a catheter into the bladder for a routine urinary drainage much more effectively than in the past since they are able to observe the entire insertion process visually through the eyepiece of the instrument as it is being performed. The ability to observe visually what is taking place fulfills a long-felt need, since by using the invention it is no longer necessary to merely shove the catheter blindly through the urethra; the invention makes it possible to do so under direct vision. Moreover, the relatively simple optical system and viewing cable 102, besides being flexible so that it can negotiate curves is much less expensive than a cystoscope which can cost in the neighborhood of $5,000.00 to $15,000.00. The use of the invention when applied in the field of veterinary medicine may provide an even greater visual advantage than with human patients since in that case no verbal communication is possible. The visual advantage is therefore often of critical importance.

If, during an insertion, an obstruction is observed, the operator by noting the nature of blockage present is better able to steer the tip of the catheter around it. In most situations the catheter can be passed the rest of the way into the bladder without further problems. However, if a serious blockage is encountered, the loss of time is minimized since the visualization by the operator will enable the urologist to pinpoint the blockage location by means of the centimeter marks (FIG. 10) indicating the distance from the penile glans or the urethral meatus, or the urologist can be told in advance something about the nature of the problem. At the same time patient comfort is improved, as is the safety of the procedure by avoiding the possibility of false passage or other injury that might otherwise take place. The invention greatly improves catheter placement through the urethra because ability to view the procedure as it is carried out provides much more positive control by the operator.

If desired, the operator can begin intubation by passing the catheter 12 conventionally, i.e., without the flexible viewing shaft 102 in place and introduce it all or part way unless a problem is encountered, and at that point insert the fiberoptic viewing cable 102. The invention can be used in virtually all urinary catheter placements which are now inserted blindly, in the neighborhood of 150,000 insertions per day in the U.S. It is particularly useful for problematic insertions, e.g., an injured patient who is suffering from pelvic injury and is bleeding from the penis. Insertion of the catheter under those conditions can be carried out much more safely with the present invention because it allows placement under vision. Any blood that may obscure the field can be flushed out by introducing saline through the opening 38. Moreover, any patient having a relatively high score on the American Urologic Association Symptom Index can be more safely intubated using the present invention.

While a so called "three-way" catheter has been shown in the Figures, it will be understood that if no retention within the bladder or flushing of the tip is required, the ducts 29 and 36 can be eliminated.

The invention substantially reduces the burden placed on "physician extenders" (R.N.'s, physician assistants and technicians), decreases physician involvement, alleviating the extreme shortage of board certified urologists. It also speeds the rectification of urinary retention in the bladder, as well as other urinary tract disorders, reduces the chance of urinary tract infections, iatrogenic trauma and patient pain. Rapid training of physician extenders can be accomplished by utilizing many visual aids currently available, thus raising healthcare efficiency and reducing costs by showing the P.E.'s how to negotiate common obstructions.

A teaching model of this invention can be fabricated so that a direct vision electronic image from the viewer 100 can be cabled to a CRT or DVD projector in real time for group training in medical schools and diverse specialties and subspecialties or physician extenders. If desired, an image sequence can be recorded for later replay. This modification of the invention can be used for remote relay for diagnosis or diagnosis confirmation via satellite relay. The two parties can be miles apart or hundreds of miles apart and faithful electronic images can be sent. Currently, most NASA manned missions include a physician. An ER surgeon or trauma surgeon is therefore able to supervise and make medical decisions using the invention. The physician can obtain diagnosis confirmation or prime diagnosis in this precision manner.

Moreover, inventory problems with catheter insertion areas such as bedsides, emergency rooms, clinics, physicians' offices, ambulances and paramedics, etc. are minimal as few catheter sizes utilizing the invention need be maintained to serve the entire adult male/female population that might be encountered. The same applies to pediatric patients. Since the catheter is under visual control of the placer at all times, false passage and other possible trauma is avoided by permitting circumnavigation of virtually any impediment to thereby provide rapid passage to the bladder.

Many variations are possible. For example, a void valve (not shown) can be provided at the proximal end of the lumen 18 for controlling urine flow from the bladder 46 into a disposable bag. The term viewer is used broadly herein to include electronic image transmission from the viewing port 104 to the eyepiece.

Other variations of the present invention within the scope of the appended claims will be apparent to those skilled in the art once the principles described herein are understood.

What is claimed is:

1. A urethral intubation apparatus for urethral placement into the bladder of a human or animal comprising, a urinary catheter formed from a flexible biocompatible polymeric material and having a central lumen extending the length thereof, said catheter having an opening centered at the distal end thereof in alignment with the longitudinal axis of the catheter and communicating with the lumen, a viewing instrument including a flexible direct vision illumination and viewing cable with a generally dome-shaped distal end that is constructed and arranged to have a sliding fit within the lumen of the catheter when mounted therein, an objective viewing port at a distal end of the cable for viewing the urethra when the distal end thereof is proximate the opening at the end of the catheter in an operating position to provide viewing through the catheter, at least one element within the cable for transmitting light through the cable to the distal end thereof to illuminate the inside of the urethra, the catheter is devoid of a shoulder stop at the distal end thereof so as to enable the distal end of the viewing instrument to extend beyond the opening for allowing a) viewing while inserting the catheter into the urethra and b) the dome-shaped end of the viewing instrument forming a contoured surface for contact with the urethra to facilitate the insertion of the catheter into the urethra, a viewer operatively associated with the viewing port for allowing observation of an image transmitted from the viewing port to enable the urethra ahead of the catheter to be seen while the catheter is being inserted into the urethra.

2. The apparatus of claim 1 wherein a distal end portion of the catheter is tapered to a smaller size proceeding toward the opening at the distal end thereof.

3. The apparatus of claim 1 wherein the catheter has a retention balloon positioned proximally of a tapered end portion thereon and an inflation duct communicating therewith.

4. The apparatus of claim 1 wherein the catheter has a retention balloon thereon and an inflation duct communicating therewith and the catheter has a longitudinally extending duct for introducing fluid into the urethra proximally of said balloon such that the balloon traps fluid between the catheter and the wall of the urethra.

5. The apparatus of claim 1 wherein the instrument is releasably held in said operating position within the catheter by a retainer and the retainer is constructed to hold the distal end of the cable proximate the opening at the end of the catheter.

6. The apparatus of claim 1 including visible indicia on the catheter for determining the distance the catheter has been inserted into the urethra.

7. A urethral intubation apparatus for urethral placement into the bladder of a human or animal comprising, a urinary catheter formed from a flexible biocompatible polymeric material and having a central lumen extending the length thereof, said catheter having an opening centered at the distal end thereof in alignment with the longitudinal axis of the catheter and communicating with the lumen, a viewing instrument including a flexible direct vision illumination and viewing cable that is constructed and arranged to have a sliding fit within the lumen of the catheter when mounted therein, an objective viewing port at a distal end of the cable for viewing the urethra when the distal end thereof is proximate the opening at the end of the catheter in an operating position to provide viewing through the catheter, at least one element within the cable for transmitting light through the cable to the distal end thereof to illuminate the inside of the urethra, a viewer operatively associated with the viewing port for allowing observation of an image transmitted from the viewing port to enable the urethra ahead of the catheter to be seen while the catheter is being inserted into the urethra a retainer is provided for releasably locking the cable in a select position within the lumen of the catheter wherein the distal end of the viewing instrument extends beyond the opening and the distal end of the instrument is smoothly contoured to provide a dome-shaped end thereon and the outer surface of the catheter is curved centrally adjacent the distal opening so as to be aligned generally with an adjacent contour at the distal end of the cable.

8. A urethral intubation apparatus for urethral placement into the bladder of a human or animal comprising, a urinary catheter formed from a flexible biocompatible polymeric material and having a central lumen extending the length thereof, said catheter having an opening centered at the distal end thereof in alignment with the longitudinal axis of the catheter and communicating with the lumen, a viewing instrument including a flexible direct vision illumination and viewing cable that is constructed and arranged to have a sliding fit within the lumen of the catheter when mounted therein, an objective viewing port at a distal end of the cable for viewing the urethra when the distal end thereof is proximate the opening at the end of the catheter in an operating position to provide viewing through the catheter, at least one element within the cable for transmitting an image through the cable to the distal end thereof to illuminate the inside of the urethra, a viewer operatively associated with the viewing port for allowing observation of an image transmitted from the viewing port to enable the urethra ahead of the catheter to be seen while the catheter is being inserted into the urethra, the instrument is releasably held in said operating position within the catheter by a retainer, the retainer is constructed to hold the distal end of the cable proximate the opening at the end of the catheter and, the instrument is constructed to releasably hold the cable in a second position for enabling the surface of the body tissue of the patient to be viewed when the body tissue of the patient or an obstruction contacts the distal end of the catheter.

9. In a flexible urinary catheter having a retention balloon at a distal end thereof for holding the catheter in the bladder following insertion, and a longitudinally extending lumen that has a central distal opening aligned with the longitudinal axis of the catheter, the improvement comprising, a removable viewing instrument having an elongated flexible optical shaft sized to slide into the catheter, a retainer for temporarily holding the shaft in selected position within the catheter with a viewing port at a distal end of the shaft positioned to receive an image of a portion of the urethra at the distal end of the catheter and said retainer being releasable in two opposite directions for allowing the flexible shaft to a) be moved proximally to enable the shaft to be removed from the catheter following placement of the catheter within the urethra and b) moved distally from said selected position.

10. The apparatus according to claim 9 wherein the flexible shaft is slideable within the lumen to a plurality of selected positions therein for moving a distal tip of the shaft relative to a distal opening at the end of the lumen.

11. The apparatus of claim 9 wherein the distal tip of the shaft has a smoothly contoured curved end surface that tapers centrally proceeding toward a distal tip thereof and the viewing port is located centrally therein.

12. In a flexible urinary catheter having a retention balloon at a distal end thereof for holding the catheter in the bladder following insertion, and a longitudinally extending lumen that has a central distal opening aligned with the longitudinal axis of the catheter, the improvement comprising, a removable viewing instrument having an elongated flexible fiberoptical shaft sized to slide into the catheter, a retainer for temporarily holding the shaft within the catheter with a viewing port at a distal end of the shaft positioned to receive an image of a portion of the urethra at the distal end of the catheter and said retainer being releasable for allowing the flexible shaft to be removed from the catheter following placement of the catheter within the urethra and a portion of the wall of the catheter adjacent the distal opening is tapered to cooperate with a curved distal surface of the instrument to form a substantially continuous composite curved surface shaped to facilitate a simultaneous insertion of the catheter and the instrument while in said selected position therein.

13. A method of facilitating insertion of a urinary catheter into the bladder of a human patient or animal comprising, placing a viewing instrument having a flexible shaft portion into a central lumen of a urinary catheter with a viewing port at a distal end of the instrument located at a distal end of the catheter, positioning the viewing port in a selected position beyond a distal end of the urinary catheter a selected distance such that the distal ends of the shaft and the catheter together form a composite tip for negotiating obstructions within the urethra, maintaining the port at the selected distance relative to the catheter during insertion wherein the distal ends thereof are proximate one another, whereby viewing the urethra through the instrument is permitted while the catheter is being inserted and thereafter withdrawing the instrument from the catheter while allowing the catheter to remain in place within the urethra.

14. The method of claim 13 including releasably retaining the shaft of the instrument for sliding movement within the lumen of the catheter between a plurality of predetermined positions.

15. The method of claim 13 including the step of providing a retainer between the catheter and the viewing instrument for holding the instrument in a selected position within the lumen of the catheter during placement of the catheter into the urethra.

16. A method of facilitating insertion of a urinary catheter into the bladder of a human patient or animal comprising, placing a viewing instrument having a flexible shaft portion into a central lumen of a urinary catheter with a viewing port at a distal end of the instrument located at a distal end of the catheter such that the distal ends of the shaft and the catheter together form a composite tip for negotiating obstructions within the urethra, maintaining the shaft in a selected position within the catheter during insertion wherein the distal ends thereof are proximate one another, placing the instrument in a first viewing position wherein the distal end of the instrument extends a predetermined distance beyond the opening at the distal end of the lumen for viewing and negotiating obstructions within the urethra, whereby viewing the urethra through the instrument is possible while the catheter is being inserted, moving the instrument to a second retracted position within the lumen of the catheter to enhance viewing ahead of the catheter and thereafter withdrawing the instrument from the catheter while allowing the catheter to remain in place within the urethra.

17. A surgical instrument for facilitating examination or for performing a surgical operation on the body of a patient, said instrument comprising, a flexible multiple use working sheath for insertion into a body cavity at the beginning of a surgical procedure, said sheath having an elongated tubular body with a central longitudinal lumen of sufficient size to accommodate elongated surgical devices or viewing devices that are inserted through the lumen of the sheath into the body of a patient, said lumen having an opening at a proximal and distal end thereof, a removable obturator for being placed in the lumen of the sheath to provide stiffness for the instrument so as to facilitate the insertion of the working sheath into the body of the patient, said instrument being adapted to be placed during use percutaneously or through a body passage into a body cavity within the body of the patient and remaining substantially stationary until the examination or procedure is complete, such that while remaining in place the obturator can be removed from the working sheath and one or more of said devices can be passed successively through the lumen into the body through the sheath, said sheath thereby serving as a single insertion instrument which provides an artificial protective lining in a body opening through which it is passed to minimize tissue trauma while reducing discomfort or pain for the patient during the passage or said devices therethrough and a grasp member having a high friction external surface thereon is provided at a proximal end of said working sheath for manipulating the sheath during use.

18. A surgical instrument for facilitating examination or for performing a surgical operation on the body of a patient, said instrument comprising, a flexible multiple use working sheath for insertion into a body cavity at the beginning of a surgical procedure, said sheath having an elongated tubular body with a central longitudinal lumen of sufficient size to accommodate elongated surgical devices or viewing devices that are inserted through the lumen of the sheath into the body of a patient, said lumen having an opening at a proximal and distal end thereof, a removable obturator for being placed in the lumen of the sheath to provide stiffness for the instrument so as to facilitate the insertion of the working sheath into the body of the patient, said instrument being adapted to be placed during use percutaneously or through a body passage into a body cavity within the body of the patient and remaining substantially stationary until the examination or procedure is complete, such that while remaining in place the obturator can be removed from the working sheath and one or more of said devices can be passed successively through the lumen into the body through the sheath, said sheath thereby serving as a single insertion instrument which provides an artificial protective lining in a body opening through which it is passed to minimize tissue trauma while reducing discomfort or pain for the patient during the passage of said devices therethrough and the removable obturator comprises a tube formed from a stiff material having a plurality of members positioned therein that help prevent the obturator from collapsing when external pressure is applied to the wall of the obturator and a closure member at each end thereof.

19. The instrument of claim 18 wherein said instrument includes a pair of peripheral longitudinally extending ducts, one such duct communicates with an inflatable circumferentially extending retention balloon at the distal end of the instrument, and the other of said peripheral ducts communicates with an outlet opening positioned proximate to the retention balloon for introducing a liquid anesthetic or medication or the like into the body of the patient such that the balloon traps the liquid between the catheter and the body opening.

20. The instrument of claim 19 wherein each of said peripheral ducts has a check valve communicating therewith at a proximal end thereof.

21. The instrument of claim 18 wherein the obturator contains a longitudinally extending fiberoptic bundle for illuminating or viewing said body cavity.

22. The instrument of claim 18 wherein the members comprise members for the transmission of an image through said tube to a viewer.

23. The instrument of claim 22 wherein the members comprise a fiberoptic bundle.

24. A surgical instrument for facilitating examination or for performing a surgical operation on the body of a patient, said instrument comprising, a flexible multiple use working sheath for insertion into a body cavity at the beginning of a surgical procedure, said sheath having an elongated tubular body with a central longitudinal lumen of sufficient size to accommodate elongated surgical devices or viewing devices that are inserted through the lumen of the sheath into the body of a patient, said lumen having an opening at a proximal and distal end thereof, a removable obturator for being placed in the lumen of the sheath to provide stiffness for the instrument so as to facilitate the insertion of the working sheath into the body of the patient, said instrument being adapted to be placed during use percutaneously or through a body passage into a body cavity within the body of the patient and remaining substantially stationary until the examination or procedure is complete, such that while remaining in place the obturator can be removed from the working sheath and one or more of said devices can be passed successively through the lumen into the body through the sheath, said sheath thereby serving as a single insertion instrument which provides an artificial protective lining in a body opening through which it is passed to minimize tissue trauma while reducing discomfort or pain for the patient during the passage or said devices therethrough and the sheath includes a longitudinally extending separation line defined by a line of weakness that facilitates progressive splitting open of the sheath when one of said devices that is larger than the internal diameter of the sheath is passed through the lumen thereof.

25. A urethral intubation apparatus for urethral placement into the bladder of a human or animal comprising, a urinary catheter formed from a flexible biocompatible polymeric material and having a central lumen extending the length thereof, said catheter having a distal opening centered at the distal end thereof in alignment with the longitudinal axis of the catheter and communicating with the lumen, a viewing instrument including a flexible illumination cable with a generally dome-shaped distal end that is constructed and arranged fit removably within the lumen of the catheter and to be inserted into the urethra while located within the catheter, said cable transmitting light energy during use from the distal end of the cable to illuminate the inside of the urethra adjacent the distal opening in the catheter, an objective viewing port at the distal end of the cable to permit viewing of the urethra when the distal end of the cable is proximate the opening at the distal end of the catheter during insertion or removal of the catheter from the urethra and, the catheter is devoid of a shoulder stop so as to enable the distal end of the viewing instrument to extend beyond the opening, the dome-shaped distal end of the viewing instrument is in contact with the urethra during insertion therein and a viewer that is operatively associated to receive an image from the viewing port to enable the urethra adjacent of the catheter to be viewed by an operator while the catheter is being inserted or removed from the urethra.

26. The apparatus of claim 25 wherein the dome-shaped end tapers centrally proceeding toward a free end thereof and has a first portion for transmitting said light energy and a second portion that comprises said objective viewing port.

27. The apparatus of claim 25 wherein a distal end portion of the catheter is tapered to a smaller size proceeding toward the opening at the distal end thereof.

28. The apparatus of claim 25 wherein a retainer is provided for releasably locking the cable in a select position within the lumen of the catheter in which the distal end of the viewing instrument is positioned adjacent the opening and allowing movement thereof in two opposite directions within the catheter.

29. The apparatus of claim 25 wherein the catheter has a retention balloon positioned proximate a tapered end portion thereof and an inflation duct for filling the balloon.

30. The apparatus of claim 29 wherein the catheter has a longitudinally extending duct positioned laterally of the lumen with an outlet opening proximal of the balloon for introducing fluid into the urethra such that the balloon traps the fluid between the catheter and the wall of the urethra.

31. The apparatus of claim 25 wherein the instrument is releasably held in an operating position within the catheter by a retainer and the retainer is constructed to hold the distal end of the cable proximate the distal opening at the end of the catheter.

32. A surgical instrument for facilitating examination or for performing a surgical operation on the body of a patient, said instrument comprising, a flexible multiple use working sheath for insertion into a body cavity at the beginning of a surgical procedure, said sheath having an elongated tubular body with a central longitudinal lumen of sufficient size to accommodate an elongated surgical device, removable obturator to provide stiffness for the instrument so as to facilitate the insertion of the working sheath into the body of the patient, or a viewing device for insertion through the lumen of the sheath into the body of a patient, said lumen having an opening at a proximal and distal end thereof, said instrument being adapted to be placed during use percutaneously or through a body passage into a body cavity within the body of the patient and remaining substantially stationary until the examination or procedure is complete, such that while remaining in place the obturator can be removed from the working sheath and one or more of said devices can be passed successively through the lumen into the body through the sheath, said sheath thereby serving as a single insertion instrument which provides an artificial protective lining in a body opening through which it is passed to minimize tissue trauma while reducing discomfort or pain for the patient during the passage of said devices therethrough, said instrument including a grasping surface portion at the proximal end of the sheath for holding the sheath so as to make the sheath easier to grip onto as the sheath is being manipulated.

33. A method of facilitating insertion of a urinary catheter into the bladder of a human patient or animal comprising, providing a urinary catheter formed from a flexible biocompatible polymeric material and having a lumen with an opening at a distal end thereof, placing a viewing instrument having a flexible shaft portion into the lumen of the catheter with a viewing port at a distal end of the instrument located at a distal end of the catheter, extending the viewing port beyond the opening at the distal end of the urinary catheter, using the viewing port of the instrument as a tip for negotiating obstructions within the urethra, maintaining the viewing port proximate the distal opening of the catheter to enable the urethra to be seen during insertion of the catheter and the viewing instrument into the urethra, viewing the urethra through the instrument during at least a portion of the time that the catheter is being inserted and thereafter withdrawing the instrument from the catheter while allowing the catheter to remain in place within the urethra.

34. The method of claim 33 including the steps of, providing the flexible shaft of the instrument with at least one steering cable and, bending the flexible shaft thereby so as to guide the tip through the urethra or around obstructions therein while viewing the patient through said port.

* * * * *